US005701349A

United States Patent [19]

Sano et al.

[11] Patent Number: 5,701,349

[45] Date of Patent: Dec. 23, 1997

[54] ACTIVE VIBRATION CONTROLLER

[75] Inventors: Hisashi Sano; Sou Nakamura; Hideshi Sawada, all of Wako; Shuichi Adachi; Hideki Kasuya, both of Utsunomiya, all of Japan

[73] Assignee: Hokda Giken Kogyo Kabushiki Kaisha, Tokyo, Japan

[21] Appl. No.: 476,332

[22] Filed: Jun. 7, 1995

[30] Foreign Application Priority Data

Jul. 14, 1994 [JP] Japan .................................... 6-162458

[51] Int. Cl.$^6$ ............................ A61F 11/06; H03B 29/00

[52] U.S. Cl. ................................................ 381/71; 381/86

[58] Field of Search ......................................... 381/71, 94

[56] References Cited

U.S. PATENT DOCUMENTS

| | | | |
|---|---|---|---|
| 5,022,082 | 6/1991 | Eriksson et al. | 381/71 |
| 5,170,433 | 12/1992 | Elliot et al. . | |
| 5,361,303 | 11/1994 | Eatwell | 381/71 |
| 5,384,853 | 1/1995 | Kinoshita et al. | 381/71 |
| 5,410,605 | 4/1995 | Sawada et al. | 381/71 |
| 5,410,606 | 4/1995 | Imai et al. | 381/71 |
| 5,416,845 | 5/1995 | Shen | 381/71 |

FOREIGN PATENT DOCUMENTS

WO 88/02912 4/1989 WIPO .

OTHER PUBLICATIONS

Extract from the dissertation of Vehicle Technique (vol. 45, No. 12, 1991) entitled "The Development of an Active Noise Control System for Vehicles" with the abridged English translation thereof.

"The Development of the Nissan Active Noise Control System" which is an abstract from Nissan Giho No. 30 (1991-12).

"Application of Active Attenuation to Car Booming Noise" which is an abstract from Mitsubishi Motors Technical Review (1992 No. 4).

"Active Control on Vehicle Booming Noise" publisher and publication date unknown, no english translation.

*Primary Examiner*—Curtis Kuntz
*Assistant Examiner*—Ping W. Lee

[57] ABSTRACT

An active vibration controller includes acceleration detectors for generating output signals on the basis of vibrations of a vehicle, speakers provided in a vehicle's cabin, microphones provided in the vehicle's cabin for receiving generated sounds from the speakers and road noises generated on the basis of running of the vehicle, and adaptive digital filters using output signals from the acceleration detectors as inputs for controlling filter factors on the basis of an RLS algorithm to minimize levels of output signals from the microphones in response to output signals from the microphones and output signals from the acceleration detectors through use of a transfer function matched to the transfer function of the vehicle's cabin in a sound field between the speakers and the microphones. The controller minimized levels of output signals from the microphones by developing an applied output signal to the speakers. Thus parameters of the filter factors are adaptively updated in accordance with identified system characteristics, providing satisfactory estimation accuracy, and quick convergence to changed sensed noise to silence road noise in the vehicle's cabin.

35 Claims, 7 Drawing Sheets

ACTIVE VIBRATION CONTROLLER

BACKGROUND OF THE INVENTION

1. Field of the Invention

The present invention relates to an active vibration controller which generates vibrations (including sounds) having phases approximately opposite to automobile noise and having amplitudes approximately the same as the noise amplitudes so that the noise is substantially silenced.

2. Description of the Related Art

Known noise cancelers eliminate noise from electronic instruments by generating signals having phases approximately opposite to the phase of the noise and having amplitudes approximately the same as the noise amplitudes. Such a noise canceler has been applied to silence noise in a space of a vehicle's cabin.

It is also known, with respect to a road noise in a vehicle's cabin, to apply an adaptive digital filter which is set to have a filter factor calculated on the basis of a multiple error filtered×LMS algorithm.

Road noise is a random noise having a broad frequency band, which is generated in a vehicle's cabin when the vehicle rides on a rough road surface. Road noise most frequently arises during routine vehicle operation and is one of most uncomfortable noises in a vehicle's cabin.

A conventional active vibration controller for silencing road noise employing an adaptive digital filter is shown in FIG. 9. Namely, acceleration detectors 1A, 1B are respectively provided for the front and rear suspensions. Noise generated in the front and rear suspensions are detected and converted into electric signals which are thereafter converted into digital signals by A/D converters 2A, 2B. The converted signals are supplied to adaptive digital filters 13A, 13B included in digital signal processors comprising, for example, FIR (Finite Impulse Response) filters capable of updating filter factors in real time to perform filter processing. Outputs from the adaptive digital filters 13A, 13B are converted into analog signals by D/A converters 4A, 4B. The analog signals converted by the D/A converters 4A, 4B are amplified by amplifiers 5A, 5B, and supplied to speakers 6A, 6B.

Sounds output from the speakers 6A, 6B, and the indoor noise resulting from the suspension are received by microphones 7A, 7B, and converted into digital signals by A/D converters 8A, 8B.

Moreover, digital filters 9A, 9B are provided, which are set to have the same transfer functions as transfer functions in the vehicle's cabin between the speakers 6A, 6B and the microphone 7A and between the speakers 6A, 6B and the microphone 7B, respectively. Outputs from the A/D converters 2A, 2B are supplied to the digital filters 9A, 9B, respectively.

In order to generate outputs from the adaptive digital filters 13A, 13B having a square sum of outputs from the microphones 7A, 7B that is minimized, the outputs from the microphones 7A, 7B (converted by the A/D converters 8A, 8B) and the outputs from the digital filters 9A, 9B are used to calculate filter factors for the adaptive digital filters 13A, 13B on the basis of an LMS (Least Mean Square) algorithm. The filter factors of the adaptive digital filters 13A, 13B are updated with calculated filter factors. Thus, the square sum level of the outputs from the microphones 7A, 7B is minimized. The processing of filter factors by using such a method is called a "multiple error filtered×LMS algorithm" or more simply a "Mef×-LMS method".

The LMS algorithm is used for the calculation of the filter factors because it requires a relatively small amount of calculation.

In FIG. 9, means for performing calculation based on the LMS algorithm are functionally illustrated as LMS algorithm calculating means 11AA, 11BB.

The digital filter 9A (9B), the adaptive digital filter 13A (13B), and the LMS algorithm calculating means 11AA (11BB) are included in the digital signal processor 12A (12B). Reference numeral 10 indicates a main active vibration controller body.

When the road noise is silenced in a vehicle's cabin, it is necessary to use the adaptive algorithm because system characteristics change depending on the vehicle speed, carrying weight, age deterioration and so on. In such a viewpoint, the multiple error filtered×LMS algorithm is widely used as described above.

SUMMARY OF THE INVENTION

When the multiple error filtered×LMS algorithm is applied to the road noise, however, problems arise in that convergence is slow, and sufficient silencing of the road noise is not necessarily effected in some cases.

An object of the present invention is to provide an active vibration controller which has rapid convergence and can be also applied to silence the road noise by using a recursive least square (RLS) algorithm.

The active vibration controller according to the present invention includes one or more first vibration detectors generating reference input signals on the basis of vibrations from vibration generating sources; one or more vibration sources provided in a sound field; one or more second vibration detectors provided in the sound field for receiving vibrations in the sound field generated from the vibration sources and the vibrations from the vibration generating sources and generating error signals on the basis of differences between the vibrations; and one or more adaptive digital filters using the reference input signals and the error signals as inputs for updating filter factors in real time to minimize levels of the error signals and energize the vibration sources by using the reference input signals, so that the vibrations in the sound field from the vibration sources are reduced, wherein updating parameters for updating the filter factors are recursively updated and processed in accordance with the reference input signals.

In the active vibration controller according to the present invention, the updating parameters used for updating the filter factors are recursively updated in accordance with the reference input signals of a system to be identified. Thus, the updating parameters are updated while learning in accordance with the system actually identified, and the filter factors are optimized for every system to be identified, giving good estimation accuracy and quick convergence time.

The filter factors are updated by using instant values of the reference input signals and the error signals. The updating parameters, however, are affected by the past reference input signals. Thus, the filter factors can be estimated without calculating expected values that would require an extensive amount of calculation, so that the estimation accuracy for filter factors is improved, and the convergence time is advantageously shortened.

Further, when the past updating parameters are weighed, the degree of contribution of past data can be changed. Thus transitive influences in an initial stage of identification can be eliminated, and a time varying system can be accurately followed.

DESCRIPTION OF THE PREFERRED EMBODIMENTS

An active vibration controller according to the present invention will be described below with reference to the preferred embodiments.

Figure 1:
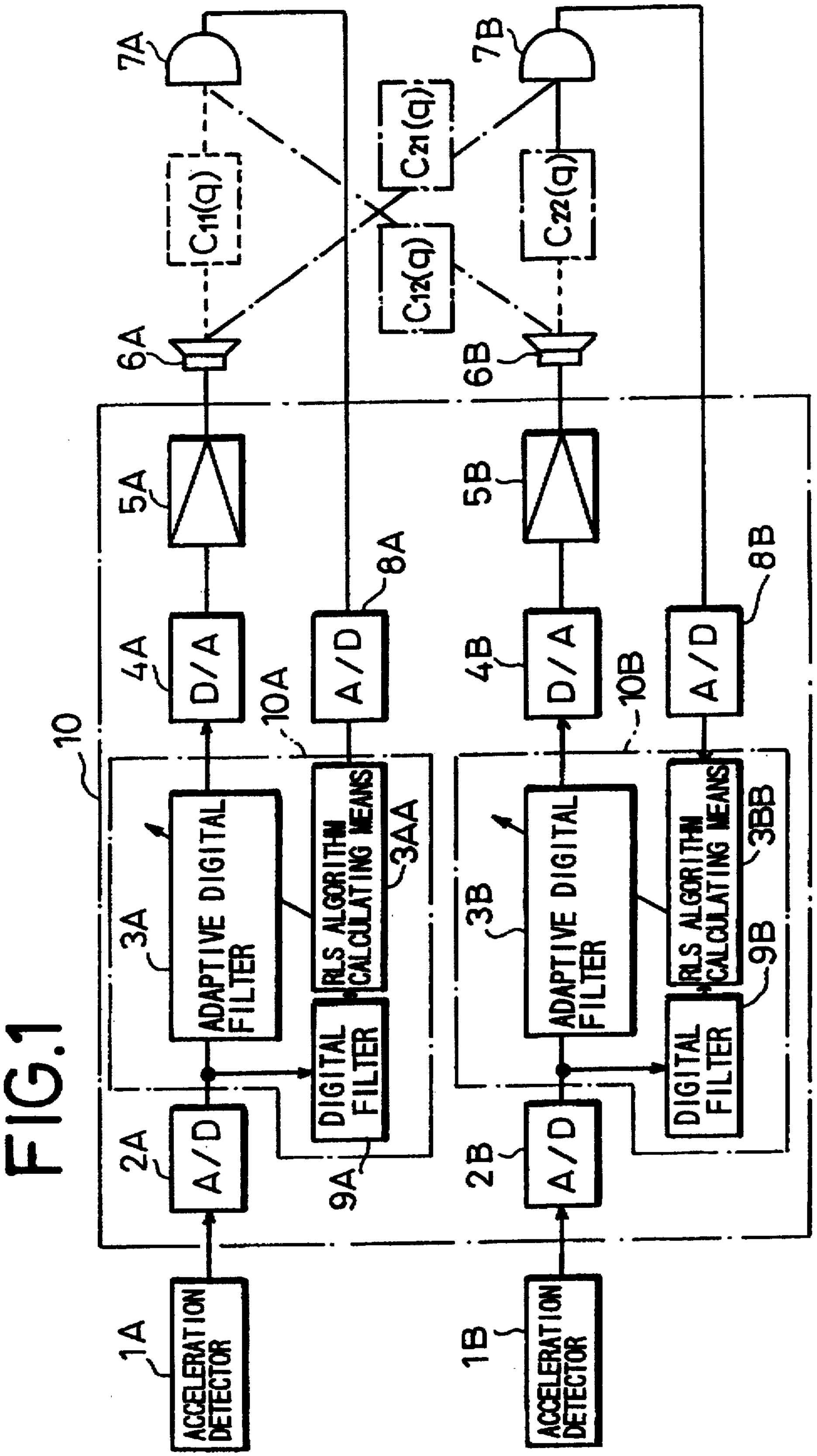
FIG. 1 is a block diagram showing the construction of one embodiment of an active vibration controller according to the present invention.
Figure 2:
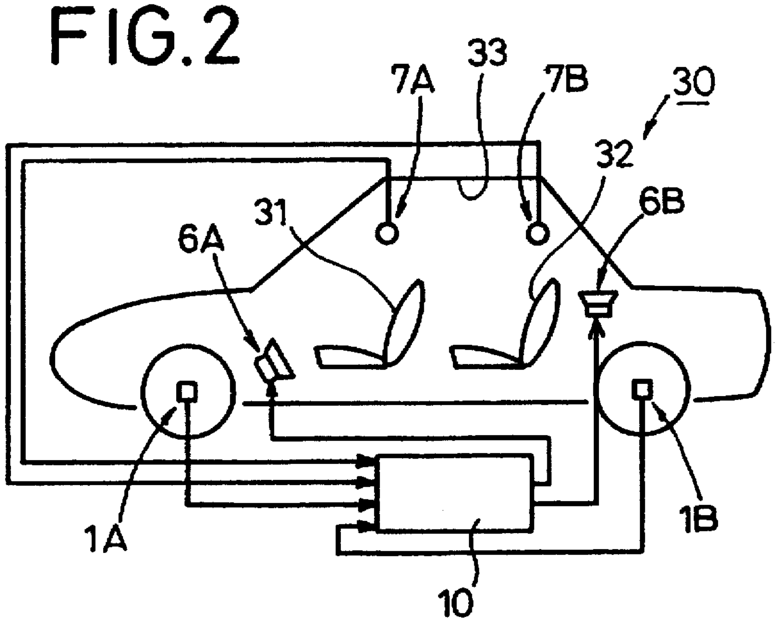
FIG. 2 is an explanatory view showing installing positions of acceleration detectors, speakers and microphones shown in FIG. 1.

FIG. 1 is a block diagram showing the construction of one embodiment of an active vibration controller according to the present invention, and FIG. 2 is an explanatory view showing installing positions of acceleration detectors, speakers and microphones shown in FIG. 1.

The active vibration controller of this embodiment is applied to silence road noise.

The active vibration controller of this embodiment includes an acceleration detector 1A, corresponding to the first vibration detector attached to either a front wheel suspension of a vehicle 30 or a body of the vehicle 30; an acceleration detector 1B, also corresponding to the first vibration detector, attached to either a rear wheel suspension of the vehicle 30 or the body of the vehicle 30; a speaker 6A serving as a vibration source installed below a driver's seat 31; a speaker 6B serving as a vibration source installed at a predetermined rear position behind a rear seat 32; microphones 7A, 7B corresponding to the second vibration detector which are mutually spaced apart by a predetermined spacing and installed on a side of a vehicle's cabin of a ceiling panel 33 so that they can monitor vibration or noise within the sound field; and a main active vibrating controller body 10 provided in the vehicle 30.

The main active vibration controller body 10 is constructed as follows. Namely, an acceleration signal detected by the acceleration detector 1A and converted into an analog electric signal is then converted into a digital signal by an A/D converter 2A. The digital acceleration signal is supplied to an adaptive digital filter 3A comprising, for example, a Finite Impulse Response (FIR) filter which is included in a digital signal processor 10A and can update filter factors in real time to perform real time filter processing. The output from adaptive digital filter 3A is converted into an analog signal by a D/A converter 4A. The analog signal converted by the D/A converter 4A is then amplified by an amplifier 5A and supplied to speaker 6A.

The other half of main active vibration controller body 10 is constructed in the same manner as described above. Namely, an acceleration signal detected by the acceleration detector 1B and converted into an analog electric signal is then converted into a digital signal by an A/D converter 2B. The digital acceleration signal is supplied to an adaptive digital filter 3B comprising, for example, an FIR filter which is included in a digital signal processor 10B and can update filter factors in real time to perform real time filter processing. An output from adaptive digital filter 3B is converted into an analog signal by a D/A converter 4B is amplified by an amplifier 5B, and the speaker 6B.

Microphone 7A receives sounds outputs from the speakers 6A, 6B and from residual road noise and converts these sounds into an electric signal which is supplied to an A/D converter 8A and converted into a digital signal.

Meanwhile, the output from the acceleration detector 1A (digitally converted by the A/D converter 2A) is supplied to a digital filter 9A. Digital filter 9A has a transfer function ($C_{11}(q)$, $C_{12}(q)$) equivalent to the transfer function of the sound field of the vehicle's cabin between the speakers 6A, 6B and the microphone 7A.

Furthermore, the filter factor of the adaptive digital filter 3A is calculated in the adaptive digital filter 3A on the basis of the output from the digital filter 9A and the output from the microphone 7A using a multiple error filtered×RLS (Recursive Least Squares) algorithm as described below such that the output from the adaptive digital filter 3A minimizes the output from the microphone 7A. The filter factor of the adaptive digital filter 3A is recursively updated to minimize the output from the microphone 7A.

In FIG. 1, a means for calculating the multiple error filtered×RLS algorithm is functionally illustrated by an RLS algorithm calculating means 3AA. The digital filter 9A, the adaptive digital filter 3A, and the RLS algorithm calculating means 3AA comprise the digital signal processor 10A.

In the same manner, an output from the microphone 7B receives sounds output from the speakers 6A, 6B and from residual road noise and converts these sounds into an electric signal which is supplied to an A/D converter 8B and converted into a digital signal.

Meanwhile, the output from the acceleration detector 1B (digitally converted by the A/D converter 2B) is supplied to a digital filter 9B. Digital filter 9B has a transfer function ($C_{21}(q)$, $C_{22}(q)$) equivalent to the transfer function of the sound field of the vehicle's cabin between the speakers (6A, 6B) and the microphone 7B.

Furthermore, the filter factor of the adaptive digital filter 3B is calculated in the adaptive digital filter 3B on the basis of the output from the digital filter 9B and the output from the microphone 7B using the multiple error filtered×RLS algorithm such that the output from the adaptive digital filter 3B minimizes the output from the microphone 7B. The filter factor of the adaptive digital filter 3B is recursively updated to minimize the output from the microphone 7B.

In FIG. 1, a means for calculating the multiple error filtered×RLS algorithm is functionally illustrated by an RLS algorithm calculating means 3BB. The digital filter 9B, the adaptive digital filter 3B, and the RLS algorithm calculating means 3BB comprise by the digital signal processor 10B.

In the case of a simple RLS algorithm, since no transfer function in the vehicle's cabin is considered from the speakers 6A, 6B to the microphones 7A, 7B, it cannot be used to silence the road noise. Thus the multiple error filtered×RLS algorithm is used to calculate the filter factor.

In this arrangement, the acceleration detectors 1A, 1B correspond to first vibration detectors; the output signals from the acceleration detectors 1A, 1B correspond to reference input signals; the speakers 6A, 6B correspond to the vibration sources; the sound field corresponds to the vehicle's cabin; and the output signals from the microphones 7A, 7B correspond to the error signals.

Next, the RLS algorithm will be explained.

Figure 3A:
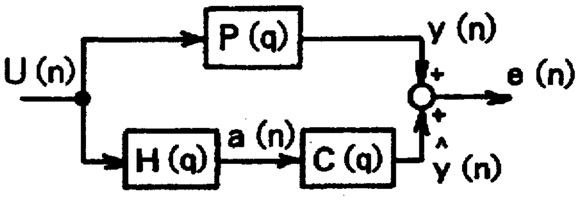
FIG. 3A is a block diagram of multiple error filtered× Recursive Least Squares (Mef×-RLS) algorithm used in the digital signal processor 10 of FIG. 2 which illustrates the operation of one embodiment of the present invention, showing an arrangement of an actual system of this embodiment.

Consider a case of K-inputs-M-outputs-L-control-points and assuming a number of input signals is K, the number of output signals is M, and the number of control points is L. In the embodiment described above, K=2 (number of acceleration detectors), M=2 (number of speakers), and L=2 (number of microphones). In FIG. 3A, a discrete system is assumed and a transfer function matrix represents a pulse transfer function matrix. In FIG. 3A, input and output relationships of the discrete time system are represented by equations (1), (2) and (3) shown below.

$$y(n)=P(q)U(n) \quad (1)$$

$$\hat{y}(n)=C(q)a(n) \quad (2)$$

$$a(n)=H(q)U(n) \quad (3)$$

In the equations above, P(q) is a transfer function matrix (unknown) from the noise source (the generating source of the road noise in the embodiment described above) to the microphone; C(q) is a transfer function matrix (known) from the speaker to the microphone; and H(q) is a transfer function matrix of the main active vibration controller body 10 (to be determined). The variable "q" is a recursive index or shift operator (namely, qU(n)=U(n+1)).

U(n) is an input signal vector, a(n) is an output signal vector of the main active vibration controller body, y(n) is an output signal vector of a transfer function matrix P(q) (transfer function matrix from the noise source to the microphone) detected by the microphone, $\hat{y}(n)$ is an output signal vector of a secondary sound source (speaker in the embodiment described above) detected by the microphone, and e(n) is an output signal vector of the microphone.

Each of the matrices and vectors P(q), C(q), H(q), U(n), a(n), y(q), $\hat{y}(n)$ and e(n) are represented by equations (4) to (11).

$$P(q)=\begin{pmatrix} P_{11}(q) & \cdots & P_{1K}(q) \\ \vdots & \ddots & \vdots \\ P_{L1}(q) & \cdots & P_{LK}(q) \end{pmatrix} \quad (4)$$

$$C(q)=\begin{pmatrix} C_{11}(q) & \cdots & C_{1M}(q) \\ \vdots & \ddots & \vdots \\ C_{L1}(q) & \cdots & C_{LM}(q) \end{pmatrix} \quad (5)$$

$$H(q)=\begin{pmatrix} H_{11}(q) & \cdots & H_{1K}(q) \\ \vdots & \ddots & \vdots \\ H_{M1}(q) & \cdots & H_{MK}(q) \end{pmatrix} \quad (6)$$

$$U(n)=(U_1(n)\ldots U_K(n))^T \quad (7)$$

$$a(n)=(a_1(n)\ldots a_M(n))^T \quad (8)$$

$$y(n)=(y_1(n)\ldots y_L(n))^T \quad (9)$$

$$\hat{y}(n)=(\hat{y}_1(n)\ldots \hat{y}_L(n))^T \quad (10)$$

$$e(n)=(e_1(n)\ldots e_L(n))^T \quad (11)$$

In accordance with FIG. 1 as mentioned above, concrete representations may be given as follows:

$$e_1=C_{11}a_1+C_{12}a_2+y_1$$

$$e_2=C_{21}a_1+C_{22}a_2+y_2$$

$$\hat{y}_1=C_{11}a_1+C_{12}a_2$$

$$\hat{y}_2=C_{21}a_1+C_{22}a_2$$

In FIG. 3A, C(q) is known, and U(n) and e(n) are observable. Thus, the transfer function matrix H(q) of the main active vibration controller body is determined. For this purpose, as can be seen from FIG. 3A, it is necessary to determine an inverse for C(q). However, since C(q) generally resides in a non-minimum phase system, it is difficult to simply determine the inverse of C(q).

As explained below, in the present invention, it is unnecessary to determine the inverse of C(q).

Figure 3B:
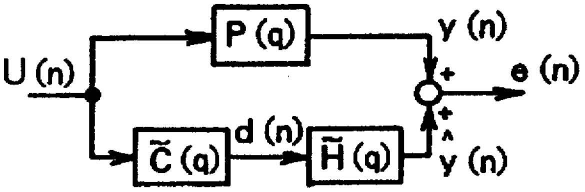
FIG. 3B is a block diagram of a Mef×-RLS, algothrim used in the digital signal processor of FIG. 2 which illustrates the operation of one embodiment of the present invention, showing an arrangement in which the order of C(q) and H(q) in FIG. 3A is exchanged.

First, as shown in FIG. 3B, the order of C(q) and H(q) is exchanged. Namely, $\hat{y}(n)$ and d(n) are represented as in equations (12) and (13).

$$\begin{aligned}\hat{y}(n) &= C(q)\,a(n) \\ &= C(q)\,H(q)\,U(n) \\ &= \tilde{H}(q)\,\tilde{C}(q)\,U(n) \\ &= \tilde{H}(q)\,d(n)\end{aligned} \quad (12)$$

where $$d(n)=\tilde{C}(q)U(n) \quad (13)$$

Now $\tilde{H}(q)$ is an L×(KML) matrix, which is represented by the following equation (14).

$$\tilde{H}(q)=\begin{pmatrix} h(q) & 0 & \cdots & 0 \\ 0 & h(q) & \cdots & 0 \\ \cdot & \cdot & & \cdot \\ \cdot & \cdot & & \cdot \\ \cdot & \cdot & & \cdot \\ 0 & 0 & \cdots & h(q) \end{pmatrix} \tag{14}$$

However, h(q) is a 1×(KM) vector, which is represented by the following equation (15).

$$h(q)=(H_{11}(q)\ldots H_{1K}(q)H_{21}(q)\ldots H_{2K}(q)\ldots H_{M1}(q)\ldots H_{MK}(q)) \tag{15}$$

Now $\tilde{C}(q)$ is a (KML)×L matrix, which is represented by the following equation (16).

$$\tilde{C}(q)=(C_{11}(q)\ldots C_{1M}(q)C_{21}(q)\ldots C_{2M}(q)\ldots C_{1m}(q)\ldots C_{L1}(q)\ldots C_{LM}(q)) \tag{16}$$

However, $C_{1m}(q)$ is a K×K matrix, which is represented by the following equation (17).

$$C_{1m}(q)=\begin{pmatrix} C_{1m}(q) & 0 & \cdots & 0 \\ 0 & C_{1m}(q) & \cdots & 0 \\ \cdot & \cdot & & \cdot \\ \cdot & \cdot & & \cdot \\ \cdot & \cdot & & \cdot \\ 0 & 0 & \cdots & C_{1m}(q) \end{pmatrix} \tag{17}$$

Herein d(n) is a (KML)×1 vector, which is represented by the following equation (18).

$$d(n)=(d_{111}(n)\ldots d_{11K}(n)\ldots d_{1M1}(n)\ldots d_{1MK}(n)\ldots d_{LM1}(n)\ldots d_{LMK}(n))^T \tag{18}$$

d(n) is called a "filtered reference" because it is a signal obtained by allowing the input signal U(n) to pass through the filter of $\tilde{C}(q)$.

Figure 3C:
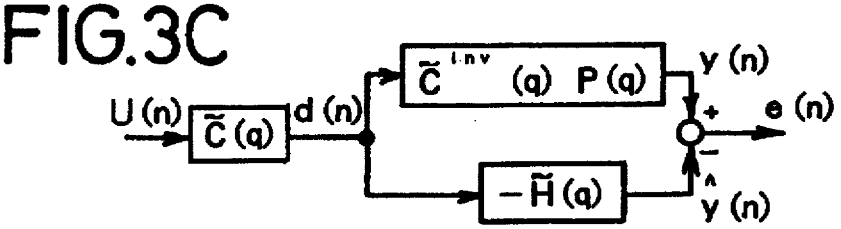
FIG. 3C shows an arrangement after equivalent conversion of FIG. 3B.

Further, the system shown in FIG. 3B is equivalently converted into a system shown in FIG. 3C. The active vibration controller shown in FIG. 3C is applied the problem of identifying unknown $\tilde{C}^{inv}(q)$, P(q) by using the observable input signal d(n) and the output signal e(n) of the microphone. Herein $\tilde{C}^{inv}(q)$, is a (KML)×K matrix, which is represented by the following equation (19).

$$\tilde{C}^{inv}(q)=(C_{11}^{inv}(q)\ldots C_{1M}^{inv}(q)C_{21}^{inv}(q)\ldots C_{2M}^{inv}(q)\ldots C_{1m}^{inv}(q)\ldots C_{L1}^{inv}(q)\ldots C_{LM}^{inv}(q)) \tag{19}$$

$\tilde{C}_{1m}^{inv}(q)$ is a K×K matrix, which is represented by the following equation (20).

$$\tilde{C}_{1m}^{inv}(q)=\begin{pmatrix} 1/C_{1m}(q) & 0 & \cdots & 0 \\ 0 & 1/C_{1m}(q) & \cdots & 0 \\ \cdot & \cdot & & \cdot \\ \cdot & \cdot & & \cdot \\ \cdot & \cdot & & \cdot \\ 0 & 0 & \cdots & 1/C_{1m}(q) \end{pmatrix} \tag{20}$$

Next, it will be explained how the multiple error filteredx RLS algorithm is applied to silence the road noise.

In FIG. 3C, using an input signal $e_1(n)$ from the first microphone, an input and output relation is represented by an FIR model as shown by the following equation (21).

$$e(n)=y(n)-\hat{y}(n) \tag{21}$$

According to the equation (21), there is given:

$$\begin{aligned} y_1(n) &= \hat{y}_1(n)+e_1(n) \\ &= b_{11,1}d_{L11}(n-1)+\ldots+b_{11,\beta}d_{111}(n-\beta)+ \\ &\quad b_{21,1}d_{121}(n-1)+\ldots+b_{21,\beta}d_{121}(n-\beta)\ldots+ \\ &\quad b_{M1,1}d_{1M1}(n-1)+\ldots+b_{M1,\beta}d_{1M1}(n-\beta)\ldots+ \\ &\quad b_{MK,1}d_{1MK}(n-1)+\ldots+b_{MK,\beta}d_{1MK}(n-\beta)\ldots+e_1(n) \end{aligned} \tag{22}$$

A parameter vector θ of a parameter b corresponding to the filter factor of the adaptive digital filter, and a data vector ϕ1 considering the transfer function in the vehicle's cabin from the speaker to the microphone are defined by equations (23) and (24).

$$\theta = (b_{11,1}\ldots b_{11,\beta}\, b_{21,1}\ldots b_{21,\beta}\ldots b_{MK,1}\ldots b_{MK,\beta})^T \tag{23}$$

$$\phi_1(n) = (d_{111}(n-1)\ldots d_{111}(n-\beta)\; d_{121}(n-1)\ldots d_{121}(n-\beta)\ldots d_{1MK}(n-1)\ldots d_{LMK}(n-\beta))^T \tag{24}$$

Thus the equation (22) is converted into equation (25).

$$y_1(n)=\phi_1(n)^T\theta+e_1(n) \tag{25}$$

Herein β is a tap number of the adaptive digital filter.

According to the equations (9), (11) and (25), the input and output relationship can be represented as the following equation (26).

$$y(n)=\phi(n)^T\theta+e(n) \tag{26}$$

Herein ϕ(n) is the following equation (27) of an MKβ×L matrix. ϕ(n) is the reference input signal passed through the digital filters 9A, 9B, however, it is also simply referred to as "reference input signal" below.

$$\phi(n)=(\phi_1(n)\ldots\phi_L(n)) \tag{27}$$

According to the above, the index of performance of the least square algorithm is represented by equation (28).

$$\begin{aligned} J(N) &= \frac{1}{N}\sum_{t=1}^{N} e(t)^T e(t) \\ &= \frac{1}{N}\sum_{t=1}^{N} (y(t)-\phi(t)^T\theta)^T(y(t)-\phi(t)^T\theta) \end{aligned} \tag{28}$$

Herein N indicates a total number of data, and n indicates the nth position in a data sequence.

A normal equation (29) for determining the parameter vector θ is obtained by differentiating J(N) for the parameter vector θ to be regarded as 0 vector.

$$R(N)\hat{\theta}(N)=f(N) \tag{29}$$

Herein R(N) is an MKβ×MKβ matrix, and f(N) is an MKβ×1 vector, which are represented by equations (30) and (31), respectively.

$$R(N)=\frac{1}{N}\sum_{t=1}^{N}\phi(t)\phi(t)^T \tag{30}$$

$$f(N)=\frac{1}{N}\sum_{t=1}^{N}\phi(t)y(t) \tag{31}$$

The RLS method is a method to solve the normal equation of the equation (29) by using a lemma of the inverse matrix.

Recursive solutions are represented by the following equations (32) and (33).

$$\hat{\theta}(n)=\hat{\theta}(n-1)+P(n)\phi(n)e(n) \tag{32}$$

$$P(n)=P(n-1)-P(n-1)\phi(n)\cdot[1+\phi(n)^T P(n-1)\phi(n)]^{-1}\cdot\phi(n)^T P(n-1) \tag{33}$$

Herein P(n) is a covariance matrix of MKβ×MKβ, which is the covariance matrix of an estimation error of the parameter vector θ, I is a unit matrix and the equations (32) and (33) are formulated by the filtered reference. This method is called "multiple error filtered×RLS algorithm" ("Mef×-RLS method") similar to the multiple error filtered× LMS algorithm. P(n) is also referred to as "updating parameter" below.

Next, it will be explained how the equations (32) and (33) have been derived from the equation (29).

The equation (29) is solved for $\hat{\theta}$(n) as in the following equation (34).

$$\hat{\theta}(N)=R(N)^{-1}f(N) \tag{34}$$

A method for recursive calculation therefor is derived.

A detailed representation of the equation (29) is the following equation (35). The next equation (36) is obtained by multiplying the both sides of the equation (35) by N.

$$\left\{\frac{1}{N}\sum_{t=1}^{N}\phi(t)\phi(t)^T\right\}\hat{\theta}(N)=\frac{1}{N}\sum_{t=1}^{N}\phi(t)y(t) \tag{35}$$

$$\left\{\sum_{t=1}^{N}\phi(t)\phi(t)^T\right\}\hat{\theta}(N)=\sum_{t=1}^{N}\phi(t)y(t) \tag{36}$$

If P(n) is represented by the following equation (37), there is given:

$$P(n)=R(n)^{-1}\equiv\left\{\sum_{t=1}^{n}\phi(t)\phi(t)^T\right\}^{-1} \tag{37}$$

The following equation (38) is obtained from the equation (37).

$$\begin{aligned}P(n)^{-1}&=\sum_{t=1}^{n-1}\phi(t)\phi(t)^T+\phi(n)\phi(n)^T\\&=P(n-1)^{-1}+\phi(n)\phi(n)^T\end{aligned} \tag{38}$$

Herein, the equation (34), that is $\hat{\theta}$(N), is represented by the following equation (39) according to the equation (36).

$$\begin{aligned}\hat{\theta}(n)&=\left\{\sum_{t=1}^{n}\phi(t)\phi(t)^T\right\}^{-1}\sum_{t=1}^{n}\phi(t)y(t)\\&=P(n)\left\{\sum_{t=1}^{n-1}\phi(t)y(t)+\phi(n)y(n)\right\}\\&=P(n)\{P(n-1)^{-1}\hat{\theta}(n-1)+\phi(n)y(n)\}\end{aligned} \tag{39}$$

Herein only the term ϕ(n)y(n) is unknown in the right side of the equation (39). According to the equation (38), $P(n-1)^{-1}$ is represented by the following equation (40).

$$P(n-1)^{-1}=P(n)^{-1}-\phi(n)\phi(n)^T \tag{40}$$

Thus the following equation (41) is obtained if the equation (39) is substituted by the equation (40).

$$\begin{aligned}\hat{\theta}(n)&=\hat{\theta}(n-1)-P(n)\phi(n)\phi(n)^T\hat{\theta}(n-1)+P(n)\phi(n)y(n)\\&=\hat{\theta}(n-1)+P(n)\phi(n)\{y(n)-\phi(n)^T\hat{\theta}(n-1)\}\\&=\hat{\theta}(n-1)+P(n)\phi(n)e(n)\end{aligned} \tag{41}$$

All the terms of the right side of the equation (41) are known. The equation (41) is the same as the equation (32) as clarified by comparing the equation (41) with the equation (32). The equation (32) has been derived from the equation (29).

Next, the equation (33) is calculated from the equation (29).

According to the equation (38), P(n) is represented by the following equation (42).

$$P(n)=\{P(n-1)^{-1}+\phi(n)\phi(n)^T\}^{-1} \tag{42}$$

In order to avoid calculating an inverse matrix, a formula represented by the following equation (43) which is a known lemma of inverse matrix is applied to the equation (42).

$$(A+BC)^{-1}=A^{-1}-A^{-1}B(1+CA^{-1}B)^{-1}CA^{-1} \tag{43}$$

Thus the equation (42) is converted into the following equation (44).

$$P(n)=P(n-1)-P(n-1)\phi(n)\cdot[1+\phi(n)^T P(n-1)\phi(n)]^{-1}\cdot\phi(n)^T P(n-1) \tag{44}$$

As clarified by comparing the equation (44) with the equation (33), the equation (44) is the same as the equation (33). Thus the equation (33) has been derived from the equation (29).

Herein P(0)=γI>0, and γ is an initial value (value in the case of n=0), and a positive real number, and I is a unit matrix.

Figure 4A:
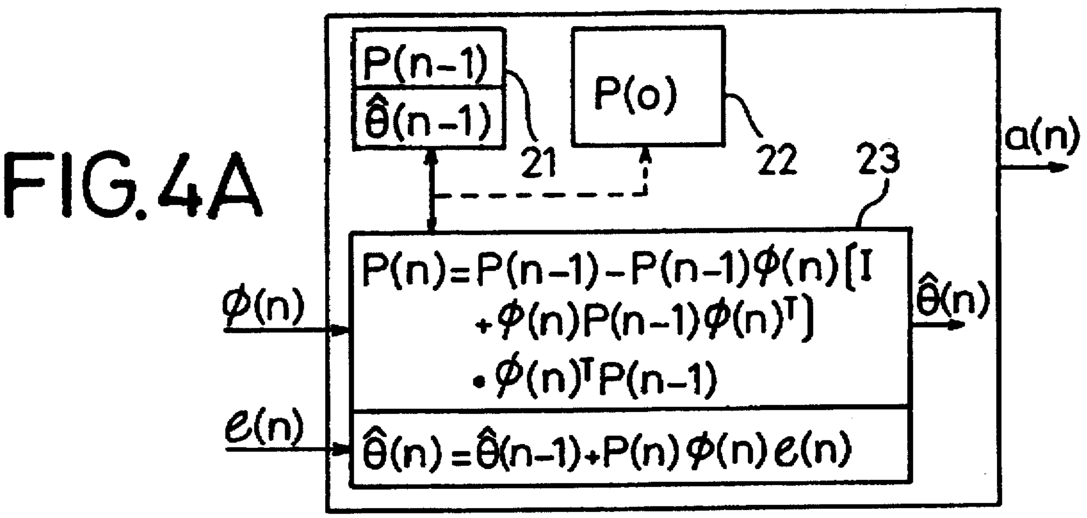
FIG. 4A is a block diagram of an arrangement in accordance with the Recursive Least Squares (RLS) method for explaining the operation of one embodiment of the present invention.

As clarified from the above, the adaptive digital filters 3A, 3B and the RLS algorithm calculating means 3AA, 3BB include a RAM 21 for storing P(n−1) and $\hat{\theta}$(n−1), a ROM 22 for storing the initial value P(0), and a calculator 23 for calculating $\hat{\theta}$(n) as shown in FIG. 4A. Instant values of e(n) and ϕ(n) and the updating parameter (P(n)) equivalent to data from the past are used for determining $\hat{\theta}$(n). Thus the estimation accuracy for $\hat{\theta}$(n) in each calculation is good, the convergence time is short, and the feature of real time operation is satisfactory although the amount of calculation is somewhat large. Further, $\hat{\theta}$(n) is always optimized for every system because the updating parameter (P(n)) is recursively updated by the reference input signal (ϕ(n)) of a system to be identified.

The Mef×-RLS method shown in the equations (32) and (33) described above is suitable for identification of a steady state system, however, it is not suitable for a case in which system characteristics change. In such a case, it is advantageous to introduce a forgetting factor.

Herein the forgetting factor is a weight by which P(n) is multiplied. The introduction of the forgetting factor thus allows the degree of contribution by the past P(n) to be changed. When the road noise is dynamic, an Mef×-RLS method with the forgetting factor is effective.

Next, the Mef×-RLS method introduced with the forgetting factor will be explained.

An index of performance J(N) introduced with a forgetting factor λ(n) (0<λ(n)<1) is represented by an equation (45).

$$J(N)=\frac{1}{N}\sum_{t=1}^{N}\lambda(N)^{N-t}\{y(t)-\phi(t)^T\theta\}^T\cdot\{y(t)-\phi(t)^T\theta\} \tag{45}$$

An equation (46) is obtained from the equation (45) by differentiating J(N) for θ to be regarded as 0 vector.

$$\left\{\frac{1}{N}\sum_{t=1}^{N}\lambda(N)^{N-t}\phi(t)\phi(t)^T\right\}\hat{\theta}(N)=\frac{1}{N}\sum_{t=1}^{N}\lambda(N)^{N-t}\phi(t)y(t) \tag{46}$$

Now if P(n) is regarded as an equation (47), $P(n)^{-1}$ is represented by an equation (48).

$$P(n)=\left\{\sum_{t=1}^{n}\lambda(n)^{n-t}\phi(t)\phi(t)^T\right\}^{-1} \tag{47}$$

$$\begin{aligned} P(n)^{-1} &= \sum_{t=1}^{n-1}\lambda(n)^{n-t}\phi(t)\phi(t)^T+\phi(n)\phi(n)^T \\ &= \lambda(n)\sum_{t=1}^{n-1}\lambda(n)^{n-1-t}\phi(t)\phi(t)^T+\phi(n)\phi(n)^T \\ &= \lambda(n)P(n-1)^{-1}+\phi(n)\phi(n)^T \end{aligned} \tag{48}$$

If the lemma of inverse matrix shown in the equation (43) is applied to equation (48), P(n) is converted into an equation (49).

$$P(n)=\frac{P(n-1)}{\lambda(n)}-\frac{P(n-1)}{\lambda(n)}\phi(n)\left[1+\phi(n)^T\frac{P(n-1)}{\lambda(n)}\phi(n)\right]^{-1}\phi(n)^T\frac{P(n-1)}{\lambda(n)} \tag{49}$$

The equation (49) is converted into an equation (50) by arranging the right side of the equation (49).

$$P(n)=\frac{1}{\lambda(n)}\left[P(n-1)-P(n-1)\phi(n)\{\lambda(n)1+\phi(n)^TP(n-1)\phi(n)\}^{-1}\phi(n)^TP(n-1)\right] \tag{50}$$

The equation (50) is an updating equation for a covariance matrix P(n) of the RLS method introduced with the forgetting factor λ(n).

The following cases (i) to (iii) may be provided in accordance with the way of selection of the forgetting factor λ(n) in the equation (50).

(i) This case employs a forgetting factor having a constant value, namely $\lambda(n)=\lambda(0<\lambda<1)$.

If $\lambda(n)=\lambda$ is given, as clarified from the equation (45), the past P(n) has a smaller weight, and the data that previously existed at a certain time before the present time is substantially discarded.

(ii) This case employs a forgetting factor that changes, wherein there is given $\lambda(n)=\lambda_0\lambda(n-1)+(1-\lambda_0)$ $(0<\lambda_0<1)$.

In this case, the forgetting factor asymptotically approaches "1". Thus transitive influences in the initial stage of identification can be eliminated. Therefore, this forgetting factor is suited for identification of a steady state system.

(iii) This case employs a forgetting factor that changes, wherein it is set as shown in an equation (51).

$$\lambda(n)=\frac{\xi(n)+\sqrt{\xi(n)^2+4\phi(n)^TP(n-1)\phi(n)}}{2} \tag{51}$$

In the equation (51), ξ(n) is a coefficient shown in an equation (52).

$$\xi(n)=1-\phi(n)^TP(n-1)\phi(n)-\frac{y(n)-\hat{\theta}(n-1)^T\phi(n)}{\sigma} \tag{52}$$

In the equation (52), σ is a parameter for determining the following speed. When σ is small, the following character is improved, and when it is large, the stability is improved. In the case of $\sigma\to\infty$, this case coincides with the RLS method.

The forgetting factor having a constant value shown in the case of (i) described above is effective for the active vibration controller for silencing the road noise because transfer characteristics of a system change depending on a road surface state, a vehicle's speed, a load according to a number of passengers, and etc.

Figure 5:
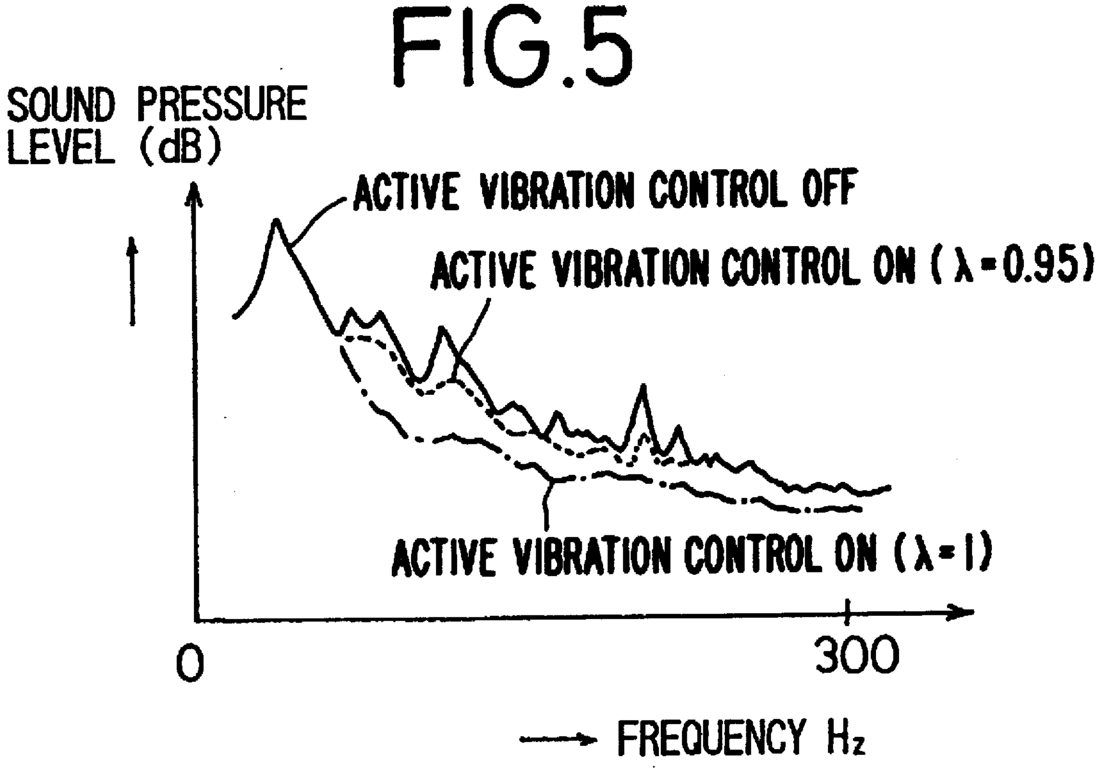
FIG. 5 is an illustration of characteristics showing the relationship between the frequency and the sound pressure level for explaining the operation of one embodiment of the present invention, a solid line shows a case in which the active vibration controller is turned off, a broken line shows a case in which the active vibration controller is turned on with forgetting factor $\lambda=1$, a dashed line shows a case in which the active vibration controller is turned on with forgetting factor $\lambda=0.95$.

The silencing performance for the road noise when the road surface changes is shown, for example, in FIG. 5. FIG. 5 shows silencing performance 5 minutes after the change of the road surface. A vehicle of 4-door sedan is used to show a relationship between the sound pressure level at the center of front seats and the frequency of the noise. A solid line shows a case in which the active vibration controller is turned off. A broken line shows a case in which the active vibration controller is turned on, with a forgetting factor λ=1, and the noise is silenced on the basis of the calculation in accordance with the RLS algorithm. A dashed line shows a case in which the active vibration controller is turned on, with a forgetting factor of a constant value of λ=0.95, and the noise is silenced on the basis of the calculation in accordance with the RLS algorithm.

Next, the convergence characteristics when the road noise is silenced are explained by comparing the conventional Mef×-LMS method and the Mef×-RLS method according to the present invention.

First, the Mef×-LMS method is derived as described. The Mef×-LMS method is an algorithm in which calculation for expected value is eliminated in updating of parameter in accordance with the steepest descent method. A parameter-updating equation in accordance with the steepest descent method is shown by equation (53).

$$\hat{\theta}(n)=\hat{\theta}(n-1)+\frac{1}{2}\mu(-\nabla J(n)) \tag{53}$$

Herein μ is a step size parameter, and ∇J(n) is a gradient vector in the equation (28). According to the equation (26), the output signal e(n) is represented by equation (54).

$$e(n)=y(n)-\phi(n)^T\theta \tag{54}$$

When the output signal e(n) is differentiated by θ, equation (55) is obtained.

$$\frac{\partial e(n)}{\partial\theta}=-\phi(n) \tag{55}$$

When the equation (28) is differentiated by θ, and the equation (55) is used, then ∇J(n) is represented by equation (56). Herein E {φ(n)e(n)} is calculation for an expected value.

$$\begin{aligned} \nabla J(n) &= \frac{\partial J(n)}{\partial\theta}=\left\{\frac{\partial}{\partial\theta}\frac{1}{n}\sum_{t=1}^{n}e(t)^Te(t)\right\} \\ &= \frac{1}{n}\sum_{t=1}^{n}\frac{\partial e(t)}{\partial\theta}\frac{\partial}{\partial e(t)}e(t)^Te(t) \\ &= \frac{1}{n}\sum_{t=1}^{n}(-\phi(t))2e(t) \\ &= -2\frac{1}{n}\sum_{t=1}^{n}\phi(t)e(t) \\ &= -2E\{\phi(n)e(n)\} \end{aligned} \tag{56}$$

When the average processing is excluded from the equation (56) to make substitution for the equation (53), equation (57) is obtained.

$$\hat{\theta}(n)=\hat{\theta}(n-1)+\mu\phi(n)e(n) \tag{57}$$

The equation (57) is a parameter-updating equation in the Mef×-LMS method, with which the factor of the adaptive digital filter is updated for every one sample.

Therefore, the time until convergence of e(n) to a minimum value changes depending on the step size parameter μ. When the step size parameter μ is not suitable, it takes a long time to achieve convergence.

Namely, when the value of the step size parameter μ is set to be large, the time required for converging e(n) to a minimum value becomes short. However, the accuracy for e(n) between the convergence value and the minimum value is low because it is impossible to achieve convergence in the vicinity of the minimum value of e(n). When the value of the step size parameter μ is set to be small, the accuracy of convergence is improved, however, the time required for achieving convergence becomes long. Examples of these relationships are shown in FIGS. 6A and 6B.

Figure 6A:
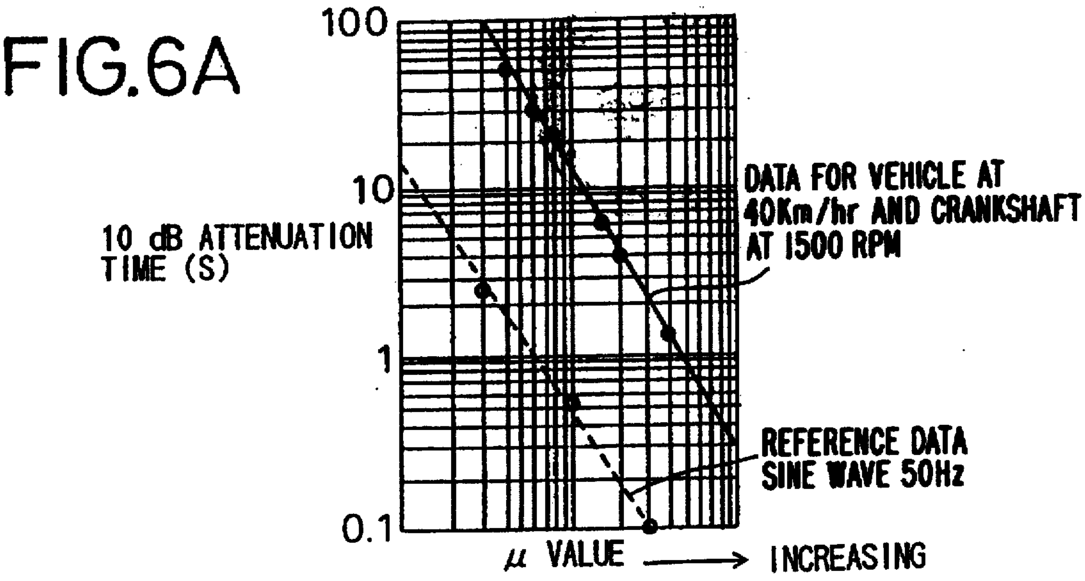
FIG. 6A is an illustration of characteristics showing the relationship between the value of step-size parameter $\mu$ and the noise attenuation time in a Mef×-LMS algorithm for explaining the operation of one embodiment of the present invention.
Figure 6B:
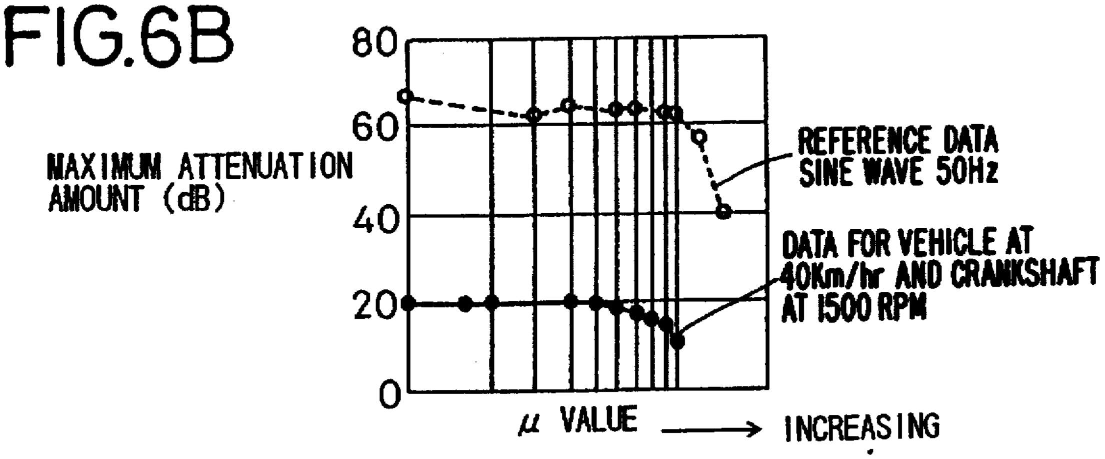
FIG. 6B is an illustration of characteristics showing the relationship between the value of step-size parameter $\mu$ and the maximum attenuation amount in an Mef×-LMS algorithm for explaining the operation of one embodiment of the present invention.

FIG. 6A shows the time (sec) required for achieving 10 dB attenuation with respect to the value of the step size parameter μ. In FIGS. 6A and 6B, a solid line indicates data in a vehicle's cabin during running with a crank shaft speed of 1500 r.p.m. and a vehicle speed of 40 km/h. A broken line represents reference data, indicating data for a sine wave of 50 Hz.

In contrast, in the Mef×-RLS method of the present invention described above, the filter factor of the adaptive digital filter is calculated based on the equations (32) and (33). Thus, the Mef×-RLS method has no necessity for setting the step size parameter μ as required by the multiple error filtered×LMS method. Accordingly, the estimation accuracy for the filter factor is high without being affected by the μ value, and the time required to converge e(n) to the minimum value is advantageously short.

Figure 7:
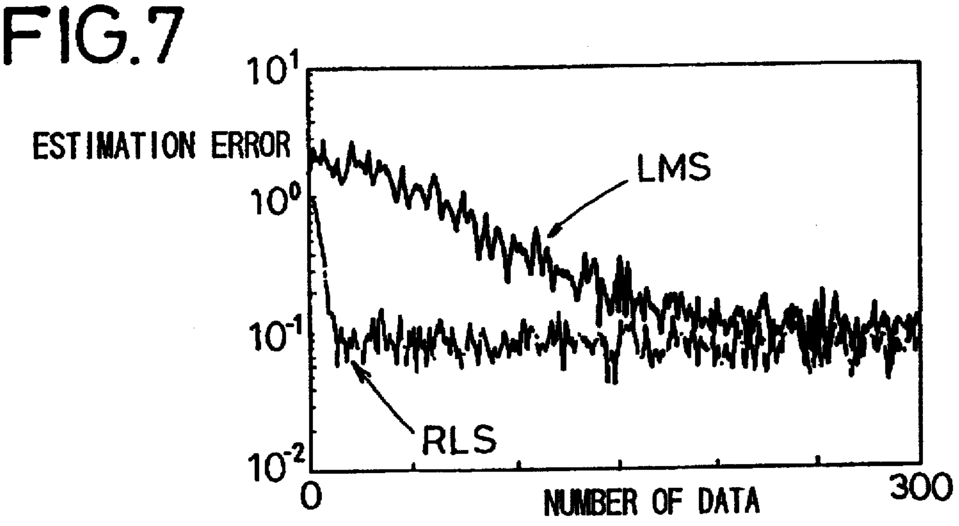
FIG. 7 is an illustration of characteristics comparing the converging speeds of Mef×-RLS and Mef×-LMS algothrims in a system such as that used in one embodiment of the present invention.

FIG. 7 illustrates the velocity of convergence with respect to the number of data N. The estimation error is constant for a small amount of data N in the Mef×-RLS method. In contrast, in the case of the Mef×-LMS method, no convergence is given without using a large number of data. Furthermore, time until convergence is longer in the Mef×-LMS method than in the Mef×-RLS method.

Figure 8A:
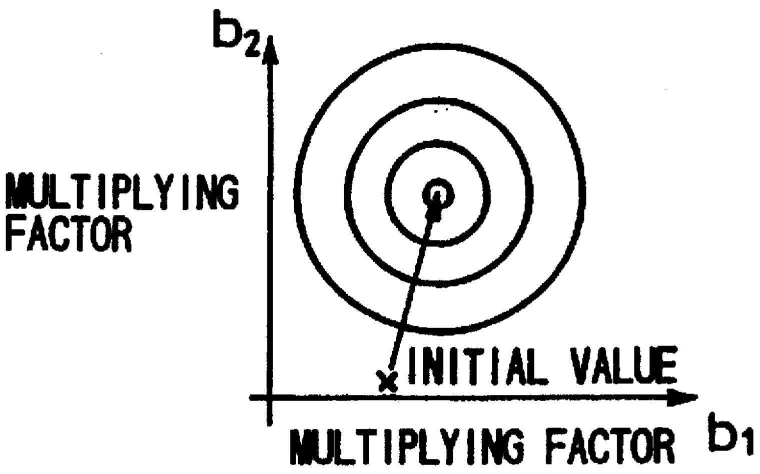
FIG. 8A is an illustrative view when the cross-sectional shape is concentric in which the index of performance J(N) represents an identical value, for explaining the operation of a conventional LMS method.
Figure 8B:
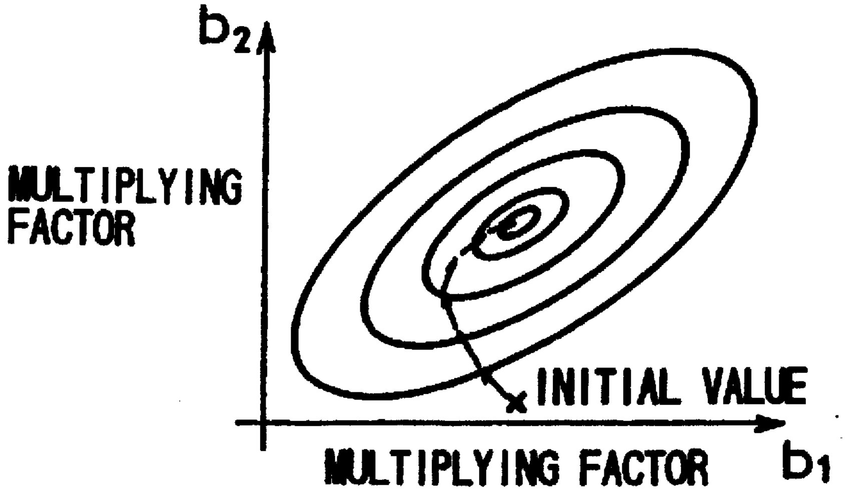
FIG. 8B is an illustrative view when the cross-sectional shape is ellipsoidal in which the index of performance J(N) represents an identical value, for explaining the operation of a conventional LMS method.
Figure 9:
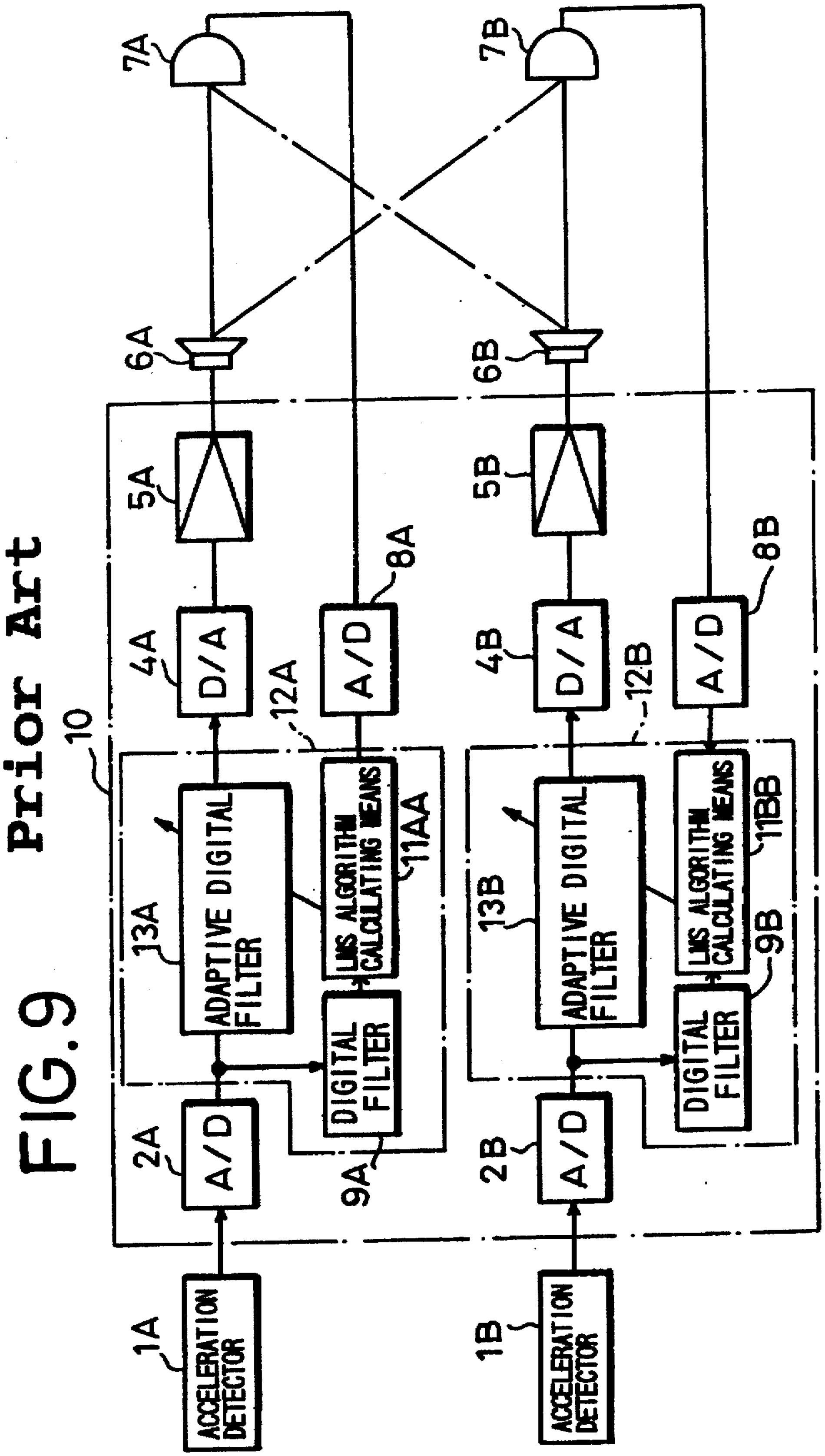
FIG. 9 Prior Art
FIG. 9 is a block diagram showing the construction of a conventional active vibration controller.

Further, in the case of the Mef×-LMS method, a system of 1-input-1-output-1-control-point may be provided, and the tap number of the adaptive digital filter may be "2" for simplification. In such a case, when the cross-sectional shape in which the index of performance J(N) of the least square method provides an identical value that is concentric as shown in FIG. 8A, the center is quickly attained irrelevant to the place of the initial value. However, when the cross-sectional shape is ellipsoidal as shown in FIG. 8B (when input signals are correlated), the Mef×-LMS which merely uses the instant value has poor accuracy and takes a long time to find an optimum point. In the preferred embodiment, specifically, in FIGS. 8A and 8B, $b_1$ and $b_2$ are multiplying factors of the multiplier comprising the adaptive digital filter with the tap number 2, which correspond to the parameter vector $\hat{\theta}$, respectively.

Next, the amount of calculation will be explained respectively for the steepest descent method, the Mef×-LMS method and the Mef×-RLS method.

In the steepest descent method, the parameter vector θ resides in the equation (53), and (∇J) in the equation (53) is as shown in the equation (56). The amount of calculation is extensive because (∇J) includes calculation for the expected value. Namely, after the active vibration controller is in an operation state, the equation (56) must be calculated by using all data. For example, when the sampling frequency is 1 kHz, the amount of data is 600,000 for 10 minutes, and the calculation time for the equation (56) becomes long.

Figure 4B:
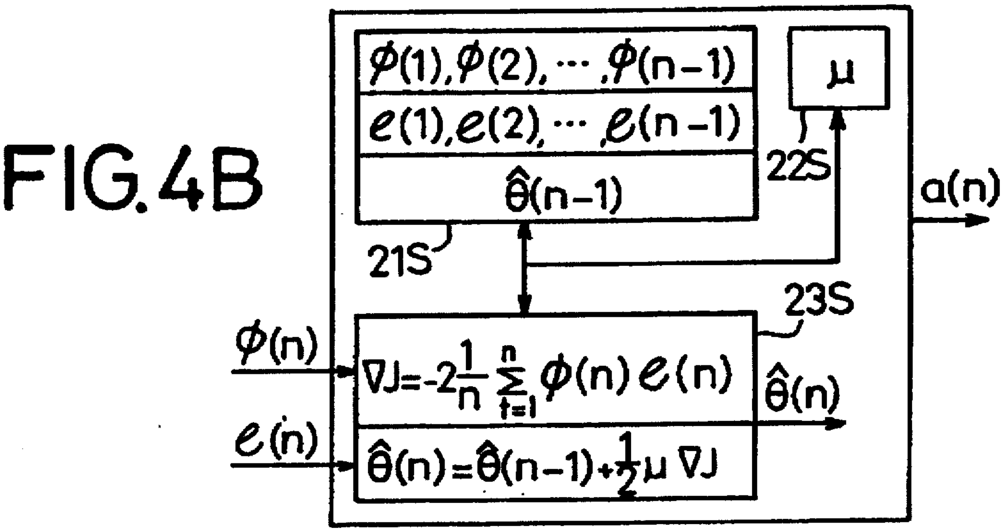
FIG. 4B is a block diagram of an arrangement in accordance with a steepest descent method for explaining the operation of one embodiment of the present invention.

Thus the steepest descent method is shown in FIG. 4B as corresponding to FIG. 4A, including a RAM 21S for storing φ(1), φ(2), . . . , φ(n−1), e(1), . . . , e(n−1) and $\hat{\theta}(n-1)$, a ROM 22S for storing the step size parameter μ, and a calculator 23S for calculating $\hat{\theta}(n)$ in accordance with the equation (53) and the following equation (58), in which data from the past φ(n), e(n) are used for calculating $\hat{\theta}(n)$. Thus the estimation accuracy for $\hat{\theta}(n)$ in each calculation is good, and the time required for convergence is short. However, the amount of calculation is extensive, and the real time operation can not be performed. Further, the estimation accuracy for $\hat{\theta}(n)$ and the convergence time are affected by selection of the step size parameter μ.

$$\nabla J = -2\frac{1}{n}\sum_{t=1}^{n}\phi(t)e(t) \tag{58}$$

Next, in the LMS method, the parameter vector θ resides in the equation (57), in which only the nth data is used among a data sequence after the active vibration controller is in an operation state. Therefore, the calculation time becomes short.

Figure 4C:
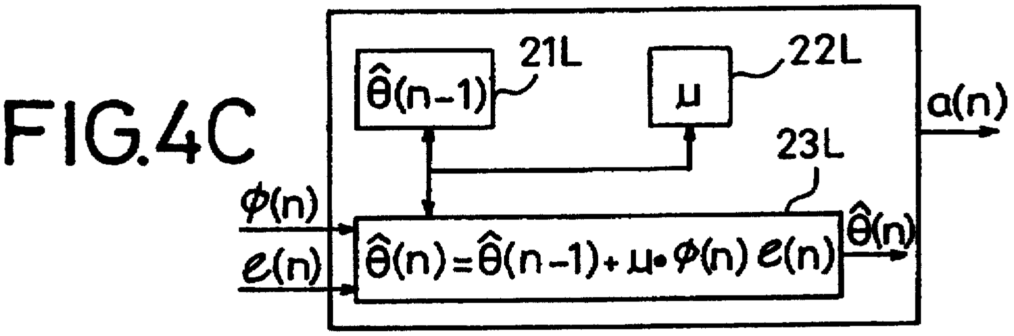
FIG. 4C is a block diagram of an arrangement in accordance with an LMS method for explaining the operation of this method.

The LMS method is shown in FIG. 4C as corresponding to FIG. 4A, including a RAM 21L for storing $\hat{\theta}(n-1)$, a ROM 22L for storing the step size parameter μ, and a calculator 23L for making calculation of the equation (57), in which the instant value φ(n) is used for determining $\hat{\theta}(n)$. Thus the amount of calculation is small, and real time operation can be achieved. However, the estimation accuracy for $\hat{\theta}(n)$ in each calculation is poor, and the convergence time is slow.

Further, the estimation accuracy for $\hat{\theta}(n)$ and the convergence time are both affected by selection of step size parameter μ.

On the contrary, in the RLS method as described above, the estimation accuracy for $\hat{\theta}(n)$ in each calculation is satisfactory, the convergence time is short, and the amount of calculation is somewhat large. However, the feature of real time operation can be achieved. Further, the updating parameter has its value is updated while learning in accordance with an identified system. Thus, $\hat{\theta}(n)$ is always optimized for each system.

As described above, according to the active vibration controller according to the present invention, the updating parameter used for updating the filter factor is recursively updated by using the reference input signal of the active vibration controller to be identified. Accordingly, the updating parameter has its value updated while learning in accordance with an identified system. Thus, the present invention has the advantages of optimizing the filter factor for each system to be identified, obtaining satisfactory estimation accuracy, and having a short convergence time.

The filter factor is updated by using instant values of the reference input signal and the error signal, however, the updating parameter is affected by the past reference input signal. Thus, the filter factor can be estimated without calculating an expected value that would require an extensive amount of calculation, resulting in improved estimation accuracy for the filter factor, and shortened convergence time.

Further, when the past updating parameter is weighed, it becomes possible to change the degree of contribution of the past data. Thus, there are also provided effects that transitive influences in the initial stage of identification can be eliminated, and a time varying system can be accurately followed.

What is claimed is:

1. An active vibration controller controlling vibration within a sound field comprising:

a first vibration detector generating reference input signals in response to detected vibrations from vibration generating sources;

a controllable vibration source provided in the sound field;

a second vibration detector provided in the sound field for receiving vibrations generated in the sound field by said controllable vibration source and by vibrations generated in said sound field from said vibration generating sources, and generating an error signal on the basis of differences between both said vibrations; and an adaptive digital filter, using the reference input signal and the error signal as inputs and having filter factors updated in real time in accordance with an updating parameter recursively updated and processed, with an initial value of the updating parameter being a predetermined positive real number, by using the reference input signals outputted from said first vibration detector, said adaptive digital filter minimizing the error signal by energizing said controllable vibration source to reduce vibrations in said sound field;

said digital filter calculating said filter factors using a recursive least squares algorithm having a forgetting factor.

2. The active vibration controller of claim 1 wherein said adaptive digital filter selects filter factors to increase the speed of convergence of the error signal.

3. The active vibration controller according to claim 1, wherein said adaptive digital filter includes a digital signal processor calculating and updating the filter factors.

4. The active vibration controller according to claim 1, wherein said updating parameter to be recursively updated is weighed.

5. The active vibration controller according to claim 1, wherein said controller uses plural first vibration detectors respectively provided at different positions on a vehicle, said first vibration detectors each being a noise detector.

6. The active vibration controller according to claim 5, wherein the vehicle includes a suspension and wherein said noise detectors detect noises generated in the suspension of the vehicle.

7. The active vibration controller according to claim 5, wherein the vehicle includes a body and wherein said noise detectors are noise detectors installed on the body of the vehicle for detecting noises generated in the body of the vehicle.

8. The active vibration controller according to claim 1, wherein said controllable vibration source includes a plurality of speakers respectively provided at different positions in a vehicle's cabin.

9. The active vibration controller according to claim 1, wherein said controller uses plural second vibration detectors respectively provided at different positions in a vehicle's cabin, said second vibration detectors are sound microphones.

10. The active vibration controller of claim 1 wherein the initial value is stored in a ROM.

11. An active vibration controller controlling vibration within a sound field comprising:

a source vibration detector positioned in a vibration transmission path between an undesired vibration source and the sound field, said source vibration detector detecting undesired vibration and developing an undesired vibration signal representing the vibration produced by said undesired vibration source;

a sound field vibration sensor disposed within the sound field, monitoring vibrations within the sound field and developing a sound field vibration signal representative of the vibrations within the sound field;

a noise path transfer function filter, operatively connected to said source vibration detector, and electronically simulating the transfer characteristic of the transmission path between the source vibration detector and the sound field, said noise path transfer function filter filtering the undesired vibration signal to develop a vibration simulation signal estimating the vibration received by the sound field from said undesired vibration source;

a cancellation vibration source disposed to introduce cancellation vibrations within the sound field to cancel vibration in the sound field originating from the undesired vibration source;

an adaptive filter filtering the undesired vibration signal to produce a vibration cancellation signal supplied to said cancellation vibration source; and means, responsive to the vibration simulation signal and the sound field vibration signal, for determining filter factors to be used by said adaptive filter to produce said vibration cancellation signal, said means for determining using a recursive least squares algorithm to determine the filter factors and recursively update the filter factors with an updating parameter, wherein the recursive least squares algorithm uses an initial value for the updating parameter which is a predetermined positive real number, and wherein said recursive least squares algorithm utilizes a forgetting factor for determining the filter factors.

12. The active vibration controller of claim 11 wherein said means for determining uses a multiple error filtered× Recursive Least Squares (Mef×-RLS) algorithm to determine the filter factors.

13. The active vibration controller of claim 12 wherein said means for determining uses the Mef×-RLS algorithm to update the filter factors in real time to minimize levels of an error signal used to produce said vibration cancellation signal.

14. The active vibration controller of claim 11 wherein said adaptive filter is a digital FIR (finite impulse response) filter.

15. The active vibration controller of claim 11 wherein said recursive least squares algorithm increases the rate of filter convergence of said adaptive filter in response to changes in the characteristics of the undesired vibration detected by said source vibration detector.

16. The active vibration controller of claim 11 wherein the forgetting factor has a constant value.

17. The active vibration controller of claim 11 wherein the forgetting factor is adaptively varied.

18. The active vibration controller of claim 11 wherein the forgetting factor is asymptotically approaches "1".

19. The active vibration controller of claim 11 wherein said adaptive filter is an adaptive digital filter with two taps.

20. The active vibration controller of claim 11 wherein said sound field is disposed within the cabin of a passenger vehicle.

21. The active vibration controller of claim 20 wherein said passenger vehicle is a wheeled passenger vehicle, said source vibration detector being suspension mounted and detecting noise generated in the vehicle's suspension.

22. The active vibration controller of claim 20 wherein said passenger vehicle is a wheeled passenger vehicle, said source vibration detector being installed on a vehicle's body for detecting noises generated in said vehicle's body.

23. The active vibration controller of claim 20 wherein said controller uses plural source vibration detectors respectively provided at different positions on the vehicle, said source vibration detectors each being a noise detector.

24. The active vibration controller of claim according to claim 11, wherein said cancellation vibration source includes plural speakers respectively provided at different positions in a vehicle's cabin.

25. The active vibration controller of claim 11 wherein the initial value is stored in a ROM.

26. A method of controlling vibration within a sound field comprising:

detecting undesired vibration at a source noise detection location disposed along a vibration transmission path between an undesired vibration source and the sound field and producing an undesired vibration signal in response thereto;

monitoring vibrations within the sound field and producing a sound field vibration signal in response thereto;

electronically simulating the transfer characteristic of the transmission path between the source noise detection location and the sound field and modifying the undesired vibration signal therewith to develop a vibration simulation signal estimating the vibration received by the sound field from said undesired vibration source;

adaptively filtering the undesired vibration signal with an adaptive filter to produce a vibration cancellation signal;

converting said vibration cancellation signal into cancellation vibrations and supplying the cancellation vibrations to the sound field to cancel the undesired vibrations in the sound field originating from the undesired vibration source;

said step of filtering including determining filter factors to be used by said adaptive filter based on said vibration simulation signal and the sound field vibration signal to produce said vibration cancellation signal by using a recursive least squares algorithm to determine the filter factors and recursively update the filter factors with an updating parameter, wherein the recursive least squares algorithm uses an initial value for the updating parameter which is a predetermined positive real number, and wherein said step of determining filter factors uses the recursive least squares algorithm while utilizing a forgetting factor in the development of the filter factors.

27. The method of claim 26 wherein said step of determining uses a multiple error filtered×Recursive Least Squares (Mef×-RLS) algorithm to determine the filter factors.

28. The method of claim 27 wherein said step of determining uses the Mef×-RLS algorithm to update the filter factors in real time to minimize levels of an error signal used to produce said vibration cancellation signal.

29. The method of claim 26 wherein said step of adaptively filtering employs a digital FIR (finite impulse response) filter.

30. The method of claim 26 wherein said step of determining uses the recursive least squares algorithm to increase the rate of filter convergence of said step of adaptive filtering in response to changes in the characteristics of the undesired vibration.

31. The method of claim 26 wherein the forgetting factor has a constant value.

32. The method of claim 26 wherein said step of determining adaptively varies the forgetting factor.

33. The method of claim 26 wherein the forgetting factor asymptotically approaches "1".

34. The method of claim 26 wherein said sound field is disposed within the cabin of a passenger vehicle.

35. The method of controlling vibration according to claim 26 further including the step of storing the initial value in a ROM.

* * * * *